United States Patent [19]

Bornzin

[11] Patent Number: 4,467,807
[45] Date of Patent: Aug. 28, 1984

[54] RATE ADAPTIVE DEMAND PACEMAKER

[75] Inventor: Gene A. Bornzin, Coon Rapids, Minn.

[73] Assignee: Medtronic, Inc., Minneapolis, Minn.

[21] Appl. No.: 323,507

[22] Filed: Nov. 23, 1981

[51] Int. Cl.³ .............................................. A61N 1/36
[52] U.S. Cl. ............................................ 128/419 PG
[58] Field of Search ................................. 128/419 PG

[56] References Cited

U.S. PATENT DOCUMENTS

| 3,648,707 | 3/1972 | Greatbatch | 128/419 PG |
| 4,052,991 | 10/1977 | Zacouto | 128/419 PG |
| 4,202,339 | 5/1980 | Wirtzfeld et al. | 128/419 PG |
| 4,313,442 | 2/1982 | Knudson | 128/419 |

OTHER PUBLICATIONS

"Relation Between QT Interval and Heart Rate New Design of Physiologically Adaptive Cardiac Pacemaker" by A. F. Rickards et al., published Jan., 1981, edition of the British Heart Journal, vol. 45, pp. 56–61.
"Frequenzsteuerung von Schrittmachern durch Bluttemperatur" by Weisswange et al., published in the Journal Deutsch Gesellschaft Fuer Kreislaufforschung, vol. 44, 1978.
Abstract entitled "An 'On Demand Pacemaker' Responsive to Respiration Rate" by Ionescu, Dept. of Cell Biology, BioMedical Engineering Unit, Institute of Biological Sciences, Splaiul Independentei 296, R-767-48-Bucharest, Rumania.
Article entitled "Ein Herzschrittmacher mit Belastungsabhangiger Frequenzregulation" by H. D. Funke, published in Biomedizinische Technik, Band 20, Heft 6/1975.
Abstract "Results, Problems and Perspectives in the Autoregulating Pacemaker" by Cammilli et al., published in the May–Jun. 1980 edition of Pace Magazine.
Article entitled "A Physiologically Controlled Cardiac Pacemaker" by J. L. Krasner et al., published in the Journal of the American Association for Medical Instrumentation, vol. 1, No. 3, Nov./Dec. 1966.
An article entitled "A New Pacemaker Autoregulating the Rate of Pacing in Relation to Metabolic Needs," by Cammilli, et al., published in the Proceedings of the 5th International Symposium, 1976 Tokyo.

Primary Examiner—William E. Kamm
Attorney, Agent, or Firm—Reed A. Duthler; John L. Rooney; Joseph F. Breimayer

[57] ABSTRACT

An implantable pacer having an effective stimulation rate which varies in response to a measured physiological parameter. Changes in the parameter to be measured must be related to physiologically required changes in heart rate. The level of oxygen within intracardiac or pulmonary artery venous blood is the preferred parameter. This parameter is measured by an oxygen sensor located on a transvenously implanted lead. As with normal demand pacers, a sensing electrode, also located on the lead, provides the pacer with an indication of whether a pacing pulse must be generated. The measured physiological parameter determines the escape interval for demand pacing. As such, a given minimum rate is determined for a given level of molecular oxygen in the intracardiac or pulmonary artery venous blood. The technique is readily employed in both ventricular and atrial-ventricular sequential modes.

7 Claims, 7 Drawing Figures

| BIT POSITION | RATE (BPM) |
|---|---|
| 30 | 120 |
| 36 | 100 |
| 40 | 90 |
| 45 | 80 |
| 50 | 72 |
| 55 | 65.4 |
| 60 | 60 |
| 65 | 55.4 |
| 70 | 51.4 |
| 75 | 48 |
| 78 | 46 |

*Fig. 6a*

| $O_2$ LEVEL (%) | BIT POSITION | 6 BIT LATCH MSB          LSB |
|---|---|---|
| 70+ | 67 | 1 0 0 0 0 1 |
| 70 | 60 | 0 1 1 1 1 0 |
| 68 | 50 | 0 1 0 1 0 0 |
| 66 | 45 | 0 0 1 1 1 1 |
| 64 | 40 | 0 0 1 0 1 0 |
| 62 | 36 | 0 0 0 1 1 0 |
| 60 | 30 | 0 0 0 0 0 0 |

*Fig. 6b*

RATE ADAPTIVE DEMAND PACEMAKER

BACKGROUND OF THE INVENTION

1. Field of the Invention

The present invention relates generally to medical devices, and more specifically relates to implantable electronic devices for muscle stimulation.

2. Description of the Prior Art

The earliest implantable pacing systems operate asynchronously to normal physiologic functions. U.S. Pat. No. 3,057,356, issued to Greatbatch, teaches such a pacer which has a fixed rate oscillator coupled to an output driver circuit. Each cycle of the fixed rate oscillator causes generation of a stimulating pulse by the output driver circuit. Designs soon incorporated the demand feature which senses natural electrical activity in the heart and generates a stimulating pulse only if none is provided physiologically within a fixed escapement period. Demand mode pacers are now the most popular and probably outnumber all other types combined. Even though later improvements provide programmability of the escape interval, the effective pacing rate of such demand pacers is non-responsive to changes in physiological requirements.

There has been considerable work done in the area of physiologically controlled pacers. Most of these devices measure some parameter and adjust the period of the oscillator in response to changes therein. An early such device is taught by Cohen in U.S. Pat. No. 3,358,690. In this special case, however, the physiologic parameter measured is instantaneous blood pressure within the right atrium. This system will apparently work well for patients having complete atrial ventricular block with properly paced atria. The Cohen approach is not likely to be effective for sick sinus syndrome, sinus/atrial block, or similar disorders.

Later physiologically controlled pacer systems have been developed which have more general application and may be categorized by the parameter measured. Krasner et al. in U.S. Pat. No. 3,593,718 teaches sensing of mechanical activity within the thorax. It is assumed that changes in respiration rate are thereby sensed. The oscillator of the pacing system has its rate controlled by changes in this parameter. Dahl, in U.S. Pat. No. 4,140,132 teaches an improved implantable sensor for determining level of a patient's physical activity for rate-controlling a pacer as taught by Krasner et al.

Bozal Gonzalez in U.S. Pat. No. 4,201,219 teaches rate control of a pacer based upon neurological activity. Electrodes imbedded in the nervous system sense electrical activity. Somehow, the amount of this electrical activity is used to control the oscillator rate of an asynchronous pacer.

By far the most promising techniques appear to involve the sensing of certain chemical parameters of venous, often intracardiac blood. Alcidi in U.S. Pat. No. 4,009,721 teaches a pacer controlled by the pH of the blood. A chronically implantable sensor determines the blood pH. The rate of an oscillator of an asynchronous pacer is controlled by the sensed pH. It has been shown that blood pH decreases during prolonged muscular exercise. Mauer et al. in U.S. Pat. No. 4,252,124 teach an improved pH sensor.

Wirtzfeld et al. in U.S. Pat. No. 4,202,339 teach a pacing system having the rate of an asynchronous oscillator controlled by the $O_2$ level of the intracardiac venous blood. As with all known prior art, physiologically controlled pacers, Wirtzfeld et al. teach what is essentially an asynchronous pacer as described by the above identified patent issued to Greatbatch, with an oscillator rate directly controlled by the measured parameter. As such, these devices are less than optimal for treating cases of partial heart block.

SUMMARY OF THE INVENTION

The present invention employs demand mode pacing with an escape interval that is determined by a measured physiological parameter. This results in a pacer system which can intermittently pace, upon demand, in hearts with partial block or sick sinus syndrome at a minimum rate that varies with physiological requirements. The preferred mode senses level of molecular oxygen within intracardiac venous blood. As the oxygen level decreases, the escape interval is shortened thus providing a higher minimum rate. Similarly, an increase in oxygen level causes a lengthened escape interval. Notice that, unlike prior art physiologically controlled pacers, the present invention treats partial heart block or sick sinus syndrome in the demand mode.

The present invention may be readily employed with sensors which measure other parameters, such as pH of blood, respiration rate, etc. Also, the present invention is readily utilized in both single chamber and two-chamber pacing modes.

BRIEF DESCRIPTION OF THE DRAWINGS

FIG. 6a is a table relating shift register position and corresponding minimum heart rate.

FIG. 6b is a table relating oxygen level to escape interval.

DETAILED DESCRIPTIONS OF THE PREFERRED EMBODIMENTS

The present invention is described herein in relation to the preferred modes of single and two-chamber pacing systems employing sensors measuring molecular oxygen level in intracardiac venous blood. Those of skill in the art, however, will be readily able to apply these teachings to devices using other pacing modes and measuring other physiologic parameters.

Figures 1, 2:
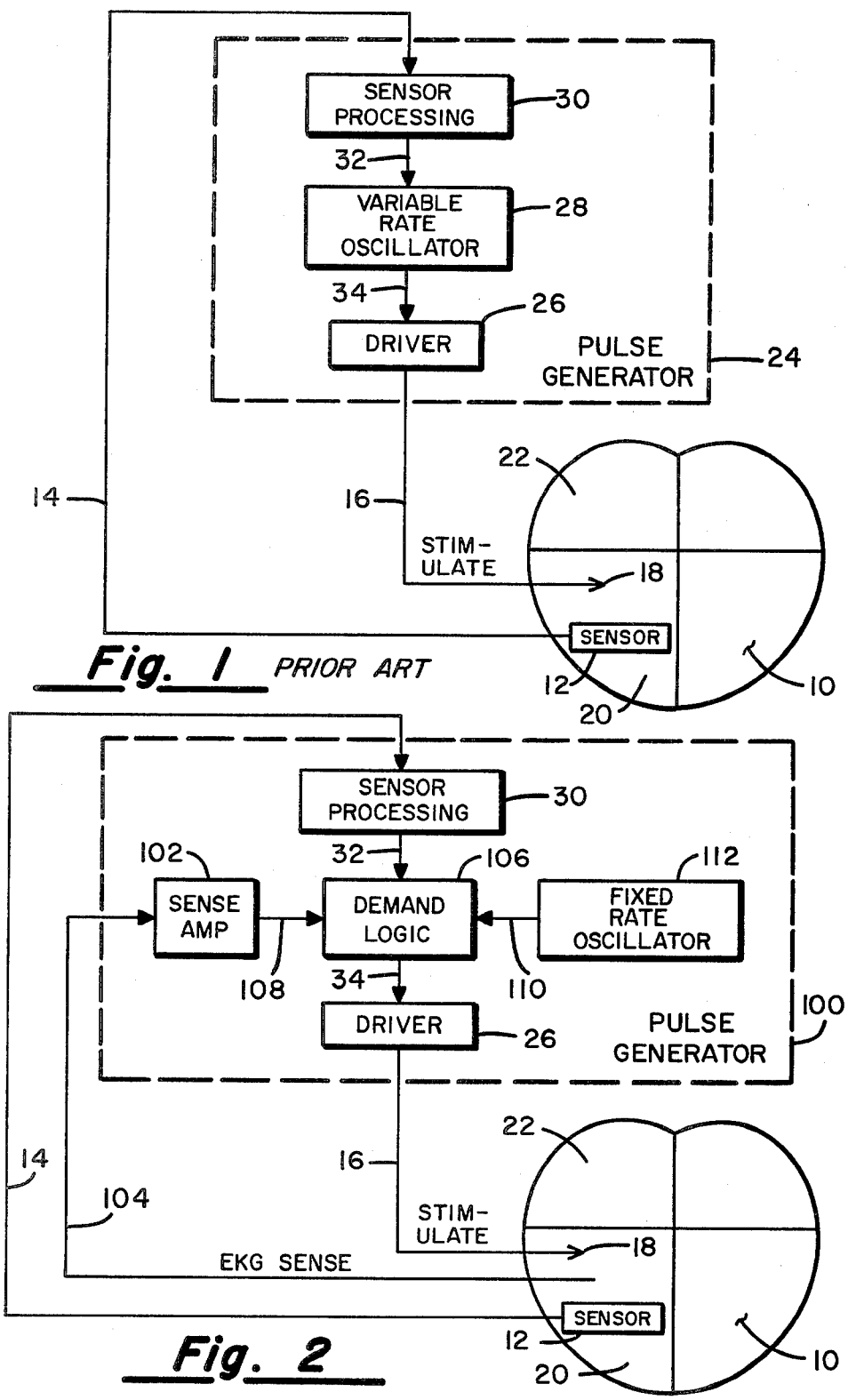
FIG. 1 is a schematic diagram of a typical prior art physiologically controlled pacing system.
FIG. 2 is a schematic diagram of a single chamber pacing system employing the present invention.

FIG. 1 is a schematic diagram of a typical prior art physiologically controlled pacing system. Sensor 12 is located within right ventricle 20 of heart 10. Sensor 12 may measure molecular oxygen level in the intracardiac blood as taught by Wirtzfeld et al., for example. Line 14 transmits the output of Sensor 12 to Sensor processing 30 of pulse generator 24. Sensor processing 30 transforms the sensed signal into a signal for controlling the rate of variable rate oscillator 28 via line 32. The output of variable rate oscillator 28 is thus a train of pulses having an interpulse period determined by the sensed parameter. Driver 26 amplifies this pulse train which is transferred to stimulating electrode 18 via conductor 16. Thus, right ventricle 20 is stimulated asynchronously of atrium 22 at a rate determined by the level of oxygen sensed by Sensor 12.

FIG. 2 is a schematic diagram of a single chamber pacing system employing the present invention. The system employs a prior art sensor 12 located within right ventricle 20 of heart 10. A probe for measuring oxygen level as disclosed in the Wirtzfeld et al. patent is preferable. However, the reader should acquaint himself with the papers: "A Miniature Fiber Optic pH Sensor Suitable for In-Vivo Application," by Goldstein et al. of the National Institute of Health and "Fiber Optic pH Probe for Physiological Use," *Analytical Chemistry*, Vol. 52, pp 864–869 (1980) by Peterson et al. Though these papers describe devices for measuring the less desirable parameter of pH, the technique of indirect measurement they propose seems promising for chronically implantable oximetry sensors as well. Sensor processing 30 converts the analog signal received from sensor 12 via line 14 into digital form and transfers a digital escape interval control signal to demand logic 106 via line 32.

Line 104 transfers an intracardiac EKG signal from right ventricle 20 to sense amp 102. The operation of sense amp 102 is common in the art. Its purpose is to examine the intracardiac EKG signal received via line 104 and determine when a QRS complex of natural origin is sensed. The output of sense amp 102 via line 108 signifies that no artificial stimulation pulse should be generated for at least one complete escape interval, since a naturally paced contraction has just occurred. U.S. Pat. No. 3,478,746 issued to Greatbatch teaches the function and operation of such a sense amplifier.

Fixed rate oscillator 112 serves as an internal clock for demand logic 106. A rate of 60 hertz is chosen as sufficiently fast and yet conserving of power. Fixed rate oscillator 112 supplies a 60 hertz pulse train to demand logic 106 via line 110.

Demand logic 106 counts an escape interval having a period established by sensor processing 30 in multiples of 1/60 second. If a pulse is not received from sense amp 102 via line 108 during that escape interval, demand logic 106 transfers a pulse enable signal to driver 26 via line 34. If a pulse is received from sense amp 102, a naturally paced contraction has occurred and the escape interval is reset without transferring a pulse enable signal to driver 26 via line 34. The important feature is that the escape interval is not fixed but is a period determined by the signal received from sensor processing 30 via line 32 which is indicative of the current oxygen level in the intracardiac blood.

Driver 26 receives the pulse enable signal from demand logic 106 via line 34 and produces a stimulation pulse which is transferred to the tissue of right ventricle 20 by conductor 16 and electrode 18. Driver 26 is preferably a capacitive discharge circuit common in the art. The design of such a circuit may be found in commonly assigned U.S. Pat. No. 4,276,883 issued to McDonald et al.

Figure 3:
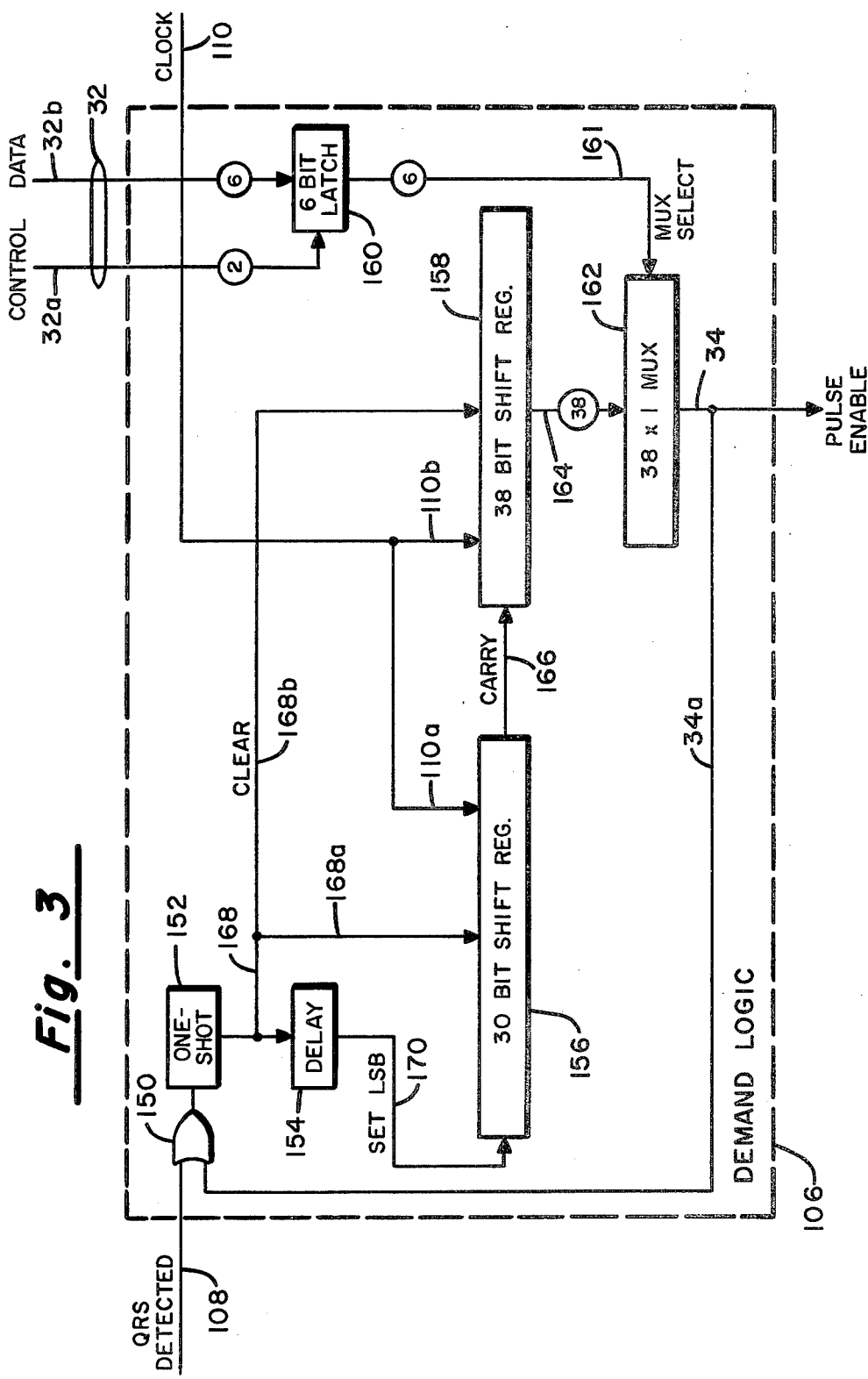
FIG. 3 is a schematic diagram of Demand Logic 106.

FIG. 3 is a detailed schematic diagram of demand logic 106. The function of demand logic 106 is to count a period of time equivalent to the escape interval for the current level of oxygen in the intracardiac blood and generate a pulse enable signal if and only if no QRS complex was detected during that escape interval. Upon generation of a pulse enable or receipt of a QRS complex detection signal, the escape interval is reset to zero.

The clock signal is a 60 hertz pulse train received from fixed rate oscillator 112 via line 110 as explained above. The clock signal serves to sequence 30 bit shift register 156 and 38 bit shift register 158. These are constructed from common CMOS monolithic part types.

OR gate 150 outputs a start reset signal whenever a QRS detect signal is received from sense amp 102 via line 108 or a pulse enable signal is generated and transmitted to OR gate 150 via line 34a. One-shot 152, being a common part type forms the start reset signal into a clear signal suitable for clearing 30 bit shift register 156 and 38 bit shift register 158. The output of one-shot 152 supplies the clear signal via lines 168a and 168b to 30 bit shift register 156 and 38 bit shift register 158, respectively.

The clear signal generated by one-shot 152 is also transferred to delay 154 which delays the pulse sufficiently long to enable 30 bit shift register 156 and 38 bit shift register 158 to be cleared. The pulse width of the clear signal is a sufficient delay time. The output of delay 154 is transferred via line 170 to set the least significant bit (LSB) position of 30 bit shift register 156. The result is that 30 bit shift register 156 and 38 bit shift register 158 are both cleared at the occurrence of a sensed QRS complex or the generation of a stimulating pulse. The LSB is next set and shifted one bit position at each pulse of the clock signal (i.e., at 60 hertz). It is easily seen that the LSB requires 500 milliseconds to shift to the carry output of 30 bit shift register 156 from whence it is propogated via line 166 to the LSB position of 38 bit shift register 158. Again, it requires 1/60 second to shift to each succeeding bit position of 38 bit shift register 158.

It would take an additional 633 milliseconds for the set bit to shift the entire length of 38 bit shift register 158. This provides a total time of 1.133 seconds to shift the entire combined length of 30 bit shift register 156 and 38 bit shift register 158. The maximum escape interval for the system is therefore 1.133 seconds, which corresponds to a heart rate of 52.9 beats per minute.

The output of each of the 38 bit positions of 38 bit shift register 158 is supplied via cable 164 to 38×1 MUX 162. By selecting the desired one of the 38 bit positions any one of 38 different escape intervals may be provided between 500 milliseconds (corresponding to 120 beats per minute) and 1.133 milliseconds (corresponding to 52.9 beats per minutes) in 1/60 second intervals. Of course, the rate of the clock signal may be increased to achieve greater resolution if required. Similarly, the length of 38 bit shift register 158 may be changed and/or the length of 30 bit shift register 156 changed to change the range of selectable escape intervals.

Common monolithic CMOS parts are used to fabricate 38×1 MUX 162. A six bit input received from six bit latch 160 via line 161 selects one of the 38 bit positions of 38 bit shift register 158 and thus determines the escape interval. If the LSB entered into 30 bit shift register 156 reaches the selected one of the 38 bit positions of 38 bit shift register 158, 38×1 MUX 162 outputs the pulse enable signal via line 34. Referring again to FIG. 2, it is seen that this results in the output of a stimulating pulse by driver 26. To ensure a minimum rate based upon the maximum escape interval, the carry output of 38 bit shift register 158 may be "ORED" with line 34. This is an optional safety measure.

Referring again to FIG. 3, selection by 38×1 MUX 162 is made by the six bit contents of six bit latch 160 which simply holds the current escape interval selector as received from sensor processing 30. A single common monolithic CMOS part is available to implement six bit latch 160.

Two control signals are required by six bit latch 160 as received by cable 32a. A first one of these signals clears the contents of six bit latch 160 and a second one is delayed and enables the six bit quantity on cable 32b to be latched into six bit latch 160.

Figure 4:
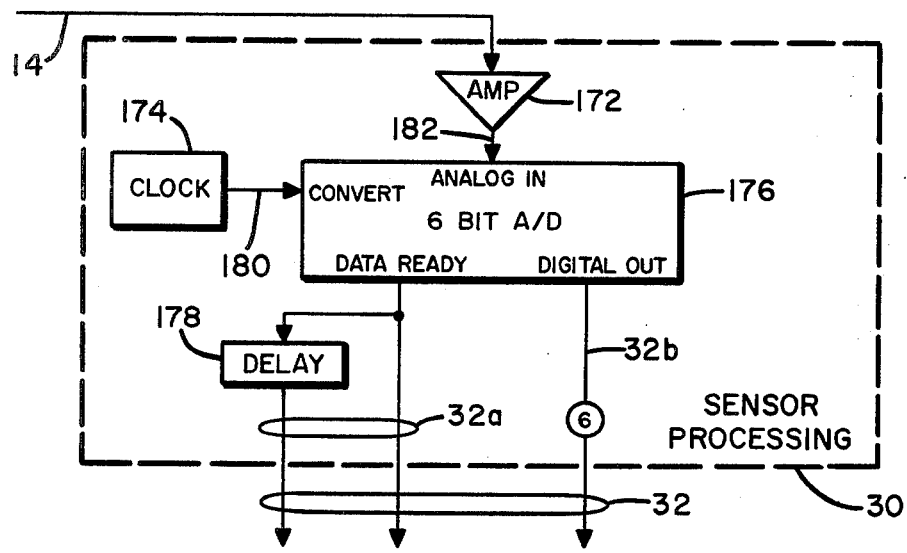
FIG. 4 is a schematic diagram of Sensor Processing 30.

FIG. 4 is a detailed schematic view of sensor processing 30. The analog sensor information is received from sensor 12 via line 14. As in Wirtzfeld et al., this is simply a signal having a voltage that is proportional to the percentage of concentration of molecular oxygen in the intracardiac venous blood. Amp 172 processes the analog signal and scales it for input to six bit A/D 176 via line 182. The processed analog signal is converted by six bit A/D 176 into a digital signal which is transmitted via cable 32b to six bit latch 160. The data ready output signal is supplied via one conductor of cable 32a to clear six bit latch 160. The data ready signal is delayed by delay 178 and sent via the other conductor of cable 32a to enable the six bit data into six bit latch 160. Clock 174 supplies the convert signal to six bit A/D 176. Clock 174 may have a very low rate (i.e., a fraction of one hertz) as the measurable changes in blood oxygen level occur slowly relative to the conversion time of six bit A/D 176 and the resulting escape interval. Fixed rate oscillator 112 or a submultiple thereof may be substituted for clock 174, but the asynchrony of a separate clock 174 is probably not detrimental and requires fewer components.

Figure 5:
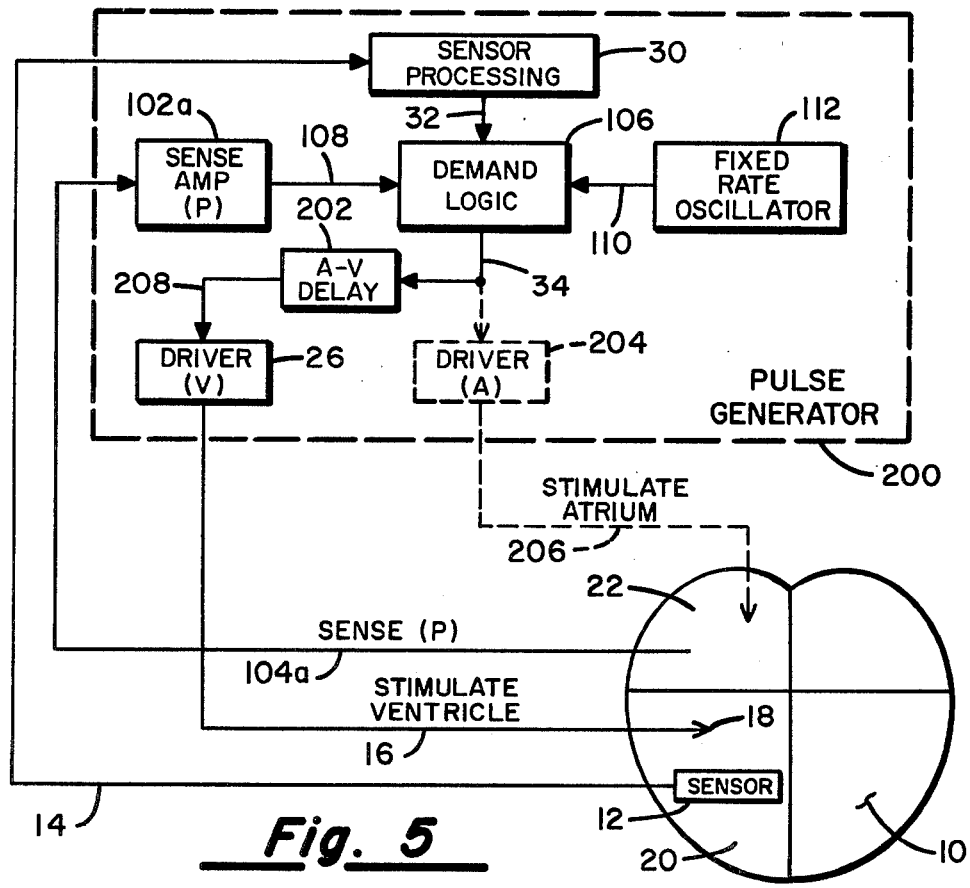
FIG. 5 is a schematic diagram of the dual-chamber pacing system employing the present invention.

FIG. 5 is an alternate embodiment of the present invention as incorporated in a two-chamber pacing system. The elements of sensor processing 30, sensor 12, electrode 18, demand logic 106 and fixed rate oscillator 112 are identical to the corresponding elements of the single chamber system and function as discussed above. Driver (v) 26 is also identical to the driver 26 of the single chamber system.

Sense amp 102 of the single chamber system is replaced by sense amp (p) 102a which is coupled via line 104a to an electrode in atrium 22. In this way sense amp 102a monitors the atrial activity rather than the ventricular activity monitored by sense amp 102 in the single chamber system (see also FIG. 2). Therefore, sense amp 102a (p) generates a p-wave sensed signal which is transferred to demand logic 106 via line 108, whenever atrium 22 is naturally paced. Sense amp (p) 102a is similar to sense amp 102 except for the enhanced sensitivity as is commmonly known in the art for p-wave sense amplifiers.

As with the single chamber system, demand logic 106 generates a pulse enable circuit whenever the escape interval period has been reached as explained above. However, in this embodiment, the escape interval is measured between p-waves rather than between r-waves. Therefore a delay is supplied by A-V delay 202 to simulate the normal atrial-to-ventricular propogation delay. This may be a fixed delay which is easily accomplished or may be a delay which is related to the pacing rate (i.e., the inverse of the escape interval) as is also known in the art.

Atrium 22 may also be artificially stimulated using driver (A) 204 and conductor 206. This option provides an effective therapy for combined intermittent sinus-atrial block, sick sinus syndrome, sinus bradycardia, and atrial-ventricular block. The optional driver (A) 204 improves hemodynamic performance by stimulating a synchronized atrial kick.

Other configurations can be readily constructed using the teachings found herein. For example, driver (V) 26 may be deleted with only driver (A) 204 in use. This configuration would readily treat intermittent sinus-atrial block or sick sinus syndrome in a patient having normal atrial-ventricular conduction.

FIG. 6a is a table showing the effective minimum heart rate in beats per minute corresponding to various selected bit positions of 30 bit shift register 156 and 38 bit shift register 158 (with the total cumulative number of bit positions shown). The maximum number of bit positions permitted by the embodiment of demand logic 106 shown in FIG. 3 is 68. However, the table of FIG. 6a is extended to 78 bit positions to show the effect of extending 38 bit shift register 158 to 48 bits.

FIG. 6b shows the relationship between a given level of molecular oxygen in the intracardiac venous blood and the output required of six bit A/D 176 to six bit latch 160. This result is obtained by adjusting the bias of amp 172 to provide a zero voltage input to six bit A/D 176 for an oxygen level of 60% of saturation. The gain of amp 172 is adjusted to drive six bit A/D 176 to approximately one-half of its maximum value for an oxygen level of 70% of saturation. As can be seen, therefore, a five bit A/D conversion is sufficient for the chosen system resolution. However, six bit devices are more commonly available. The total measured range of interest in oxygen level is between 60% and 70%. Because of the components chosen, this provides an escape interval range corresponding to 52.9 to 120 beats per minute. The system is self-limiting to remain within this range. The ideal relationship of saturation levels to escape interval can vary from patient to patient, and is preferrably programmable using an external device. Support may be readily found in the current literature to permit determination of other effective relationships.

What is claimed is:

1. A demand heart pacemaker for providing stimulating pulses to the heart at a predetermined rate in the absence of naturally occurring heartbeats comprising:

sensing means for sensing naturally occurring heart signals and generating a reset signal;

pulse generator means for generating stimulating pulses at a minimum pacing rate, including timing means for providing each stimulating pulse separated by an escape interval corresponding to the pacing rate and reset means responsive to a reset signal for resetting said timing means and restarting the escape interval;

means for measuring a physiological parameter indicative of the level of cardiac output demanded by the patient's body and for providing an escape interval modifying signal; and means responsive to the escape interval modifying signal for adjusting the escape interval to provide pacing pulses on demand at a minimum rate correlated to the cardiac output requirements of the patient.

2. A demand heart pacemaker according to claim 1 wherein said adjusting means further comprises means for decreasing the escape interval.

3. A demand heart pacemaker according to claim 1 or 2 wherein said adjusting means further comprises means for increasing the escape interval.

4. A demand heart pacemaker according to claim 1 wherein said physiological parameter is molecular oxygen level is venous blood.

5. A demand heart pacemaker according to claim 1 wherein said predetermined electrical event comprises an R-wave.

6. A demand heart pacemaker according to claim 1 wherein said predetermined electrical event comprises a P-wave.

7. A demand heart pacemaker for providing stimulating pulses to the heart at a predetermined rate in the absence of naturally occurring heartbeats, comprising:

sensing means for sensing naturally occurring electrical heart signals and for generating a reset signal in response to sensing said naturally occurring heart signals;

pulse generator means for generating stimulating pulses at a minimum pacing rate, including timing means for providing each stimulating pulse at the termination of an escape interval corresponding to the pacing rate and reset means responsive to said reset signal for resetting said timing means and restarting said escape interval;

means for measuring a chemical parameter of venous blood indicative of the level of cardiac output demanded by the patient's body and for providing an escape interval modifying signal determined by the measurement of said chemical parameter; and means responsive to the escape interval modifying signal for adjusting the escape interval to provide pacing pulses on demand at a minimum rate correlated to the cardiac output requirements of the patient.

* * * * *

REEXAMINATION CERTIFICATE (1728th)

United States Patent [19]

Bornzin

[11] B1 4,467,807

[45] Certificate Issued Jun. 30, 1992

[54] RATE ADAPTIVE DEMAND PACEMAKER

[75] Inventor: Gene A. Bornzin, Coon Rapids, Minn.

[73] Assignee: Medtronics, Inc., Minneapolis, Minn.

Reexamination Request:
No. 90/002,161, Oct. 9, 1990

Reexamination Certificate for:
Patent No.: 4,467,807
Issued: Aug. 28, 1984
Appl. No.: 323,507
Filed: Nov. 23, 1981

[51] Int. Cl.⁵ ............................................. A61N 1/365
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,648,707 | 3/1972 | Greatbatch | 128/419 P |
| 4,009,721 | 3/1977 | Alcidi | 128/419 PG |
| 4,052,991 | 10/1987 | Zacouto | 128/419 G |
| 4,201,219 | 5/1980 | Gonzalez | 128/419 PG |
| 4,228,803 | 10/1980 | Rickards | 128/419 PG |
| 4,305,396 | 12/1981 | Wittkampf | 128/419 G |
| 4,312,355 | 1/1982 | Funke | 128/419 PG |

FOREIGN PATENT DOCUMENTS

| | | | |
|---|---|---|---|
| P26093652 | 9/1977 | Fed. Rep. of Germany | 335/128 |
| 2403775 | 4/1979 | France | |

*Primary Examiner*—William E. Kamm

[57] ABSTRACT

An implantable pacer having an effective stimulation rate which varies in response to a measured physiological parameter. Changes in the parameter to be measured must be related to physiologically required changes in heart rate. The level of oxygen within intracardiac or pulmonary artery venous blood is the preferred parameter. This parameter is measured by an oxygen sensor located on a transvenously implanted lead. As with normal demand pacers, a sensing electrode, also located on the lead, provides the pacer with an indication of whether a pacing pulse must be generated. The measured physiological parameter determines the escape interval for demand pacing. As such, a given minimum rate is determined for a given level of molecular oxygen in the intracardiac or pulmonary artery venous blood. The technique is readily employed in both ventricular and atrial-ventricular sequential modes.

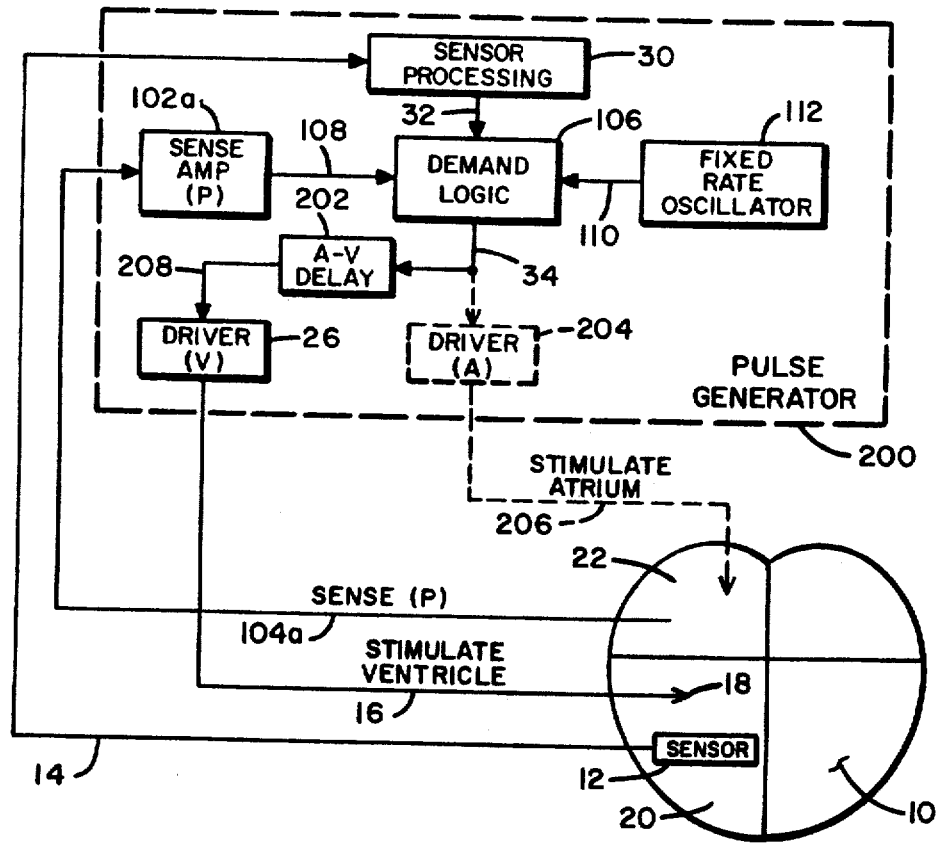

B1 4,467,807

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

The drawing figure has been changed as follows: Broken line 34 and 206 made solid ONLY THOSE PARAGRAPHS OF THE SPECIFICATION AFFECTED BY AMENDMENT ARE PRINTED HEREIN.

Column 3, lines 3-21:
FIG. 2 is a schematic diagram of a single chamber pacing system employing the present invention. The system employs a prior art sensor 12 located within right ventricle 20 of heart 10. A probe for measuring oxygen level as disclosed in the Wirzfeld et al. patent is preferable. However, the reader should acquaint himself with the papers: "A Miniature Fiber Optic pH sensor Suitable for In-Vivo Application," by Goldstein et al. of the National Institute of Health and "Fiber Optic pH Probe for Physiological Use," Analytical Chemistry, vol. 52, pp. 864-869 (1980) by Peterson et al. Though these papers described devices for measuring the less desirable parameter of pH, the technique of indirect [measuremeni] *measurement* they propose seems promising for chronically implantable oximetry sensors as well. Sensor processing 30 converts the analog signal received from sensor 12 via line 14 into digital form and transfers a digital escape interval control signal to demand logic 106 via line 32.

AS RESULT OF REEXAMINATION, IT HAS BEEN DETERMINED THAT:

The patentability of claim 7 is confirmed.

Claims 1-3 and 5 are cancelled.

Claims 4 and 6 are determined to be patentable as amended.

New claims 8-26 are added and determined to be patentable.

4. A demand heart pacemaker [according to claim 1] *for providing stimulating pulses to the heart at predetermined rate in the absence of naturally occuring heat beats comprising:*
   *sensing means for sensing naturally occurring heart signals and generating a reset signal;*
   *pulse generator means for generating stimulating pulses at a minimum pacing rate, including timing means for providing each stimulating pulse separated by an escape interval corresponding to the pacing rate and reset means responsive to a reset signal for resetting said timing means and restarting the escape interval;*
   *means for measuring a physiological parameter indicative of the level of cardiac output demanded by the patient's body and for providing an escape interval modifying signal; and*
   *means responsive to the escape interval modifying signal for adjusting the escape interval to provide pacing pulses on demand at a minimum rate correlated to the cardiac output requirements of the patient;*
   wherein said *means for measuring a* physiological parameter [is] *comprises means for measuring* molecular oxygen level [is] *in* venous blood.

6. A demand heart packemaker [according to claim 1] *for providing stimulating pulses to the heart at predetermined rate in the absence of naturally occurring heart beats comprising:*
   *sensing means for sensing naturally occurring heart signals and generating a reset signal;*
   *pulse generator means for generating stimulating pulses at a minimum pacing rate, including timing means for providing each stimulating pulse separated by an escape interval corresponding to the pacing rate and reset means responsive to a reset signal for resetting said timing means and restarting the escape interval;*
   *means for measuring a physiological parameter indicative of the level of cardiac output demanded by the patient's body and for providing an escape interval modifying signal; wherein said means for measuring a physiological parameter comprises means for measuring a parameter of venous blood; and*
   *means responsive to the escape interval modifying signal for adjusting the escape interval to provide pacing pulses on demand at a minimum rate correlated to the cardiac output requirements of the patient;*
   wherein said [predetermined electrical event comprises a P-wave] *means for sensing naturally occurring heart signals comprises means for sensing P-waves.*

8. *A demand heart pacemaker for providing stimulating pulses to the heart in the absence of naturally occurring heartbeats, comprising:*
   *sensing means for sensing naturally occurring heart signals and generating a reset signal;*
   *pulse generator means for generating stimulating pulses at a minimum rate, including timing means for providing each stimulating pulse separated by an escape interval corresponding to the pacing rate and reset means responsive to a reset signal for resetting said timing means and restarting the escape interval;*
   *means for measuring a physiological parameter indicative of the level of cardiac output demanded by the patient's body and for providing an escape interval modifying signal, said measuring means comprising sensor means for providing a signal indicative of the patient's demand for cardiac output and clock means for regularly converting said signal from said sensor means to an escape interval modifying signal; and*
   *means responsive to the escape interval modifying signal for adjusting the escape interval to provide pacing pulses on demand at a minimum rate correlated to the cardiac output requirements of the patient.*

9. *A pacemaker according to claim 6 or claim 8 wherein said means for measuring a physiologic parameter comprises means for measuring molecular oxygen level in venous blood.*

10. *A pacemaker according to claim 8 wherein said means for measuring a physiologic parameter comprises means for measuring a parameter of venous blood.*

11. A pacemaker according to claim 8 wherein said means for sensing naturally occurring heart signals comprises means for sensing R-waves.

12. A pacemaker according to claim 8 wherein said means for sensing naturally occurring heart signals comprises means for sensing P-waves.

13. A pacemaker according to claim 8 wherein said pulse generator means comprises means for generating atrial pulses for stimulating the atrium of the heart.

14. A pacemaker according to claim 13 wherein said pulse generator means comprises means for providing an A-V delay following said atrial pulses and means for generating ventricular pulses for stimulating the ventricle of the heart following said A-V delay.

15. A demand heart pacemaker for providing stimulating pulses to a patient's heart in the absence of naturally occurring heartbeats, comprising:
sensing means for sensing naturally occurring heart signals in the atrium and generating a reset signal;
pulse generator means for generating atrial stimulating pulses at a minimum rate, including timing means for providing each atrial stimulating pulse separated by an escape interval corresponding to the pacing rate and reset means responsive to a reset signal for resetting said timing means and restarting the escape interval, said pulse generator means further comprising means for providing an A-V delay following said atrial stimulating pulses and means for generating ventricular stimulating pulses following said A-V delay;
means for measuring a physiological parameter indicative of the level of cardiac output demanded by the patient's body and for providing an escape interval modifying signal; and
means responsive to the escape interval modifying signal for adjusting the escape interval to provide pacing pulses on demand at a minimum rate correlated to the cardiac output requirements of the patient; and
wherein said means for measuring a physiologic parameter comprises means for measuring a parameter of venous blood.

16. A demand heart pacemaker for providing stimulating pulses to a patient's heart in the absence of naturally occurring heartbeats, comprising:
sensing means for sensing naturally occurring heart signals in the atrium and generating a reset signal;
pulse generator means for generating atrial stimulating pulses at a minimum rate, including timing means for providing each atrial stimulating pulse separated by an escape interval corresponding to the pacing rate and reset means responsive to a reset signal for resetting said timing means and restarting the escape interval, said pulse generator means further comprising means for providing a A-V delay following said atrial stimulating pulses and means for generating ventricular stimulating pulses following said A-V delay;
means for measuring a physiological parameter indicative of the level of cardiac output demanded by the patient's body and for providing an escape interval modifying signal; and
means responsive to the escape interval modifying signal for adjusting the escape interval to provide pacing pulses on demand at a minimum rate correlated to the cardiac output requirements of the patient; and
wherein said means for measuring a physiologic parameter comprises means for measuring molecular oxygen level in venous blood.

17. A demand heart pacemaker for providing stimulating pulses to a patient's heart in the absence of naturally occurring heartbeats, comprising:
sensing means for sensing naturally occurring heart signals and generating a reset signal;
pulse generator means for generating stimulating pulses at a minimum rate, including timing means for providing each stimulating pulse separated by an escape interval corrsponding to the pacing rate, said escape interval started in response to the expiration of a previous escape interval, and reset means responsive to a reset signal for resetting said timing means and restarting the escape interval;
means for measuring a physiological parameter indicative of the level of cardiac output demanded by the patient's body and for providing an escape interval modifying signal, said measuring means comprising sensor means for providing a signal indicative of the patient's demand for cardiac output and means for regularly converting said signal from said sensor means to an escape interval modifying signal indicative of said patient's demand for cardiac output, said converting means converting said signal from said sensor both during escape intervals started by said reset signals and during escape intervals started by expiration of previous escape intervals, to provide said escape interval modifying signal indicative of the patient's demand for cardiac output; and
means responsive to the escape interval modifying signal for adjusting the escape interval to provide pacing pulses on demand at a minimum rate correlated to the cardiac output requirements of the patient.

18. A pacemaker according to claim 17 wherein said means for sensing naturally occurring heart signals comprises means for sensing R-waves.

19. A pacemaker according to claim 17 wherein said means for sensing naturally occurring heart signals comprises means for sensing P-waves.

20. A pacemaker according to claim 17 wherein said pulse generator means comprises means for generating atrial pulses for stimulating the patient's atrium.

21. A demand heart pacemaker for providing stimulating pulses to a patient's heart in the absence of naturally occurring heartbeats, comprising:
sensing means for sensing naturally occurring atrial heart signals and generating a reset signal;
pulse generator means for generating atrial stimulating pulses at a minimum rate, including timing means for providing each atrial stimulating pulse separated by an escape interval corresponding to the pacing rate and reset means responsive to a reset signal for resetting said timing means and restarting the escape interval, said pulse generator means further comprising means for providing an A-V delay following said atrial stimulating pulse and means for generating a ventricular stimulating pulse following said A-V delay;
means for measuring a physiological parameter indicative of the level of cardiac output demanded by the patient's body and means for regularly converting said signal from said sensor means to an escape interval modifying signal indicative of said patient's demand for cardiac output, said converting means converting said signal from said sensor both during escape intervals started by said reset signals and during escape intervals started by expiration of previous escape intervals, to provide said escape interval modifying signal indicative of the patient's demand for cardiac output; and means responsive to the escape interval modifying signal for adjusting the escape interval to provide pacing pulses on demand at a minimum rate correlated to the cardiac output requirements of the patient.

22. A pacemaker according to claim 17 or 21 wherein said converting means comprises a clock means for regularly triggering conversion of said signals from said sensor to escape interval modifying signals indicative of the patient's current demand for cardiac output.

23. A pacemaker according to claim 22 wherein said clock means comprises clock means for triggering conversion of said signals from said sensor means asynchronous to said timing means.

24. A pacemaker according to claim 17 or 21 wherein said means for measuring a physiologic parameter comprises means for measuring a parameter of venous blood.

25. A pacemaker according to claim 17 or 21 wherein said means for measuring a physiologic parameter comprises means for measuring molecular oxygen level in venous blood.

26. A pacemaker according to claim 21 wherein said means for providing an A-V delay comprises means for providing a fixed A-V delay.

* * * * *